United States Patent
Gao et al.

(10) Patent No.: US 6,471,840 B1
(45) Date of Patent: Oct. 29, 2002

(54) COMPOSITE SENSOR

(75) Inventors: Yunzhi Gao, Kumagaya (JP); Akira Kunimoto, Kumagaya (JP); Masaharu Hasei, Kumagaya (JP)

(73) Assignee: Kabushiki Kaisha Riken, Tokyo (JP)

( * ) Notice: Subject to any disclaimer, the term of this patent is extended or adjusted under 35 U.S.C. 154(b) by 0 days.

(21) Appl. No.: 09/622,549
(22) PCT Filed: Dec. 21, 1999
(86) PCT No.: PCT/JP99/07170
§ 371 (c)(1),
(2), (4) Date: Aug. 18, 2000
(87) PCT Pub. No.: WO00/37930
PCT Pub. Date: Jun. 29, 2000

(30) Foreign Application Priority Data

Dec. 21, 1998 (JP) .......................................... 10-362139

(51) Int. Cl.$^7$ ............................................. G01N 27/407
(52) U.S. Cl. ........................ 204/425; 204/426; 204/427; 205/781
(58) Field of Search .................................. 204/421–429

(56) References Cited

U.S. PATENT DOCUMENTS

| | | | |
|---|---|---|---|
| 5,672,811 A | * | 9/1997 | Kato et al. |
| 5,980,728 A | * | 11/1999 | Farber et al. |
| 6,045,673 A | * | 4/2000 | Kato et al. |
| 6,059,947 A | * | 5/2000 | Kato et al. |
| 6,068,747 A | * | 5/2000 | Tojo et al. |
| 6,306,271 B1 | * | 10/2001 | Kato et al. |
| 6,319,377 B1 | * | 11/2001 | Hasei et al. |
| 6,332,965 B1 | * | 12/2001 | Sugiyama et al. |

FOREIGN PATENT DOCUMENTS

EP 892265 A1 2/1999

OTHER PUBLICATIONS

U.S. patent application Ser. No. 09/191,109, Hasei et al., filed Nov. 13, 1998.

* cited by examiner

Primary Examiner—T. Tung
(74) Attorney, Agent, or Firm—Kubovcik & Kubovcik (57) ABSTRACT

A combined gas sensor of the invention is equipped with a second oxygen sensing electrode 5 active only to oxygen, which is disposed on a solid electrolyte substrate 3a such that it is directly exposed to detection gases. Sensor disorder is detected by measuring an electromotive force (signal output 2) generated between a reference electrode 7 and the second oxygen sensing electrode 5 as an oxygen concentration in an exhaust gas atmosphere, and comparing and judging the detected result with a signal output 1 corresponding to an electromotive force between a first oxygen sensing electrode 4 and the sit reference electrode 7, or with a signal output of an oxygen pump current.

15 Claims, 10 Drawing Sheets

COMPOSITE SENSOR

TECHNICAL FIELD

The present invention relates to a gas sensor, and particularly to a combined gas sensor for detecting the concentration of acid gases such as nitrogen oxides, etc. in exhaust gases and oxygen concentration in a gas atmosphere to be detected.

BACKGROUND OF THE INVENTION

Various poison gases including nitrogen oxides ($NO_x$), hydrocarbon gases (HC), sulfur oxides ($SO_x$), CO, $CO_2$, and etc., are exhausted from internal combustion engines including those of automobiles, and combustion instruments of thermal power plants, and factory plants, etc. They are called environmental gases, and severe legal regulations have been enforced to limit the emission of environmental gases. Thus, the development of a gas sensor capable of detecting the low concentrations of the exhausted environmental gases at a low cost has been demanded.

Recently, an all-solid-type gas sensor which can carry out the continuous measurement by direct insertion in exhaust gases from engines of automobiles, etc., has been watched with keen interest, and many investigations and developments thereof have been reported. The present inventors already proposed a mixed potential-type $NO_x$ sensor capable of measuring the total $NO_x$ concentrations in exhaust gases at real time. For example, in Japanese Patent Laid-Open Publication No. 201942/1999, a mixed potential-type $NO_x$ sensing electrode is disposed in a gas chamber formed by Zirconia solid electrolyte, and also a $NO_x$ converting electrode is disposed in the same chamber such that it faces to the $NO_x$ sensing electrode. That is, in this structure, $NO_x$ (NO and $NO_2$) in exhaust gases are electrochemically converted to a $NO_2$ single substance gas, and the converted $NO_2$ concentration is detected by the $NO_x$ sensing electrode as the total $NO_x$ concentration. In the embodiment of Japanese Patent Laid-Open Publication No. 201942/1999, an oxygen pump (converting pump) for converting $NO_x$ in the gas chamber to $NO_2$ and another oxygen pump for controlling the oxygen concentration in a gas chamber are disposed. Also, a reference electrode to the $NO_x$ sensing electrode described above and an oxygen sensing electrode for measuring the oxygen concentration in the gas chamber are disposed in the same gas chamber. By referring the potential of the oxygen sensing electrode due to the oxygen concentration in the gas chamber as a reference potential of the $NO_x$ sensing electrode, the output of the $NO_x$ sensor is hardly influenced even when the oxygen concentration in the gas chamber is fluctuated.

The fluctuation of the oxygen concentration is, however, large and sharp in the exhaust gases from e.g. an automobile. Therefore, in the $NO_x$ sensor element with the gas chamber structure shown in Japanese Patent Laid-Open Publication No. 201942/1999, etc., it is necessary to make the oxygen concentration in the gas chamber at a level at which interference gases such as HC, CO, etc., entering the gas chamber together with $NO_x$, are oxidized to non-interference gases. The oxygen concentration around the sensing electrode based on mixed potential should also be sustained at a substantially constant value of several percents. Accordingly, the occurrence of disorder of a system, in which the detection of the oxygen concentration in a gas chamber is carried out and the oxygen pump driving is controlled by feeding back the signal of the oxygen concentration, gives a large error to the accuracy of the sensor output. Also, as a precondition, it is necessary that the gas tightness in the gas chamber and the air duct is kept in order.

On the other hand, the temperature of the exhaust gases from automobiles is increasing more and more recently, and the gas temperature changes largely, depending on the driving states of engine thereof. Also, poison components for the electrodes are largely contained in exhaust gases, and further, the vibration of the body or the engine of automobiles is large. Thus, an improvement of the reliability of the gas sensor used in exhaust gases under such severe circumstances becomes very important.

However, in the conventional $NO_x$ sensor disclosed in Japanese Patent Laid-Open Publication No. 201942/1999, even when disorder occurs in the system in which the detection of the oxygen concentration in the gas chamber is carried out, and the oxygen pump driving is carried out by feed-back control, it was impossible to self-diagnosed diagnose whether the sensor was in order or not. Also, when the gas tightness of the gas chamber and the air duct, is lost during the use to influence the sensor output, the $NO_x$ sensor did not have any means for informing a user whether or not such is due to the sensor disorder. That is, the above-described $NO_x$ sensor has problems that when deterioration of electrodes, disorder in controlling the oxygen concentration in the gas chamber, and losing of the gas tightness of the gas chamber or the air duct occur during the use of the gas sensor, it cannot be determined that they are due to disorder of the sensor or not.

BRIEF SUMMARY OF THE INVENTION

The present invention has been made for solving the above-described problems.

According to the invention, there is provided a combined gas sensor having a structure equipped with a first gas chamber formed by an oxygen ion conductive solid electrolyte; a first gas inlet having a diffusion resistance for restricting the flow amount of gases entering the first gas chamber; a first oxygen sensing electrode active only to oxygen, which is disposed on a surface of the first electrolyte substrate inside the first gas chamber; a gas sensing electrode active to at least target gases and oxygen, which is disposed on the same surface of the first electrolyte as the first oxygen sensing electrode; a reference electrode active to oxygen, which is disposed on the first solid electrolyte substrate such that it is brought into contact with an atmospheric air separated from the first gas chamber; an oxygen pump cell for controlling oxygen concentration in the first gas chamber, of which electrodes are made of materials active only to oxygen and disposed on a second solid electrolyte substrate facing to the first solid electrolyte substrate; a gas reforming pump cell for chemically or electrochemically converting or decomposing the gases, of which a gas reforming electrode is active to oxygen and the target gases, and disposed on the second solid electrolyte substrate in the first gas chamber so as to face to the gas sensing electrode, and a gas reforming counter electrode is disposed on the second solid electrolyte substrate outside the first gas chamber such that it is brought into contact with the atmospheric air; and a second oxygen sensing electrode active only to oxygen, which is disposed on the first solid electrolyte substrate such that it is directly exposed to the detection gas atmosphere.

Furthermore, according to the invention, there is provided a combined gas sensor comprising an oxygen pump cell for controlling the oxygen concentration in the first gas chamber, of which the electrodes are made of materials active only to oxygen and disposed on the second solid electrolyte substrate facing to the first solid electrolyte substrate; and a gas reforming pump cell for chemically or electrochemically converting or decomposing the gases, of which a gas reforming electrode is active to oxygen and the target gases and disposed on the second solid electrolyte substrate in the first gas chamber so as to face to the gas sensing electrode, and a gas reforming counter electrode is disposed on the second solid electrolyte substrate outside the first gas chamber such that it is brought into contact with the atmospheric air, and characterized by having driving cell circuits wherein a DC variable power supply for controlling the oxygen concentration in the first gas chamber at a constant level by feed-back control of pumping currents for the oxygen pump cell, according to an electromotive force between the oxygen sensing electrode and the reference electrode as a signal output of the oxygen concentration in the first gas chamber, and a DC constant voltage power supply for making oxygen pumping currents of the gas reforming pump cell constant, and thus making an electrochemical decomposition or conversion amount of the target gas constant; are connected to the oxygen pump cell and the gas reforming pump cell, respectively.

According to the invention, in the gas sensor having the gas chamber formed by the oxygen ion conductive solid electrolyte, the oxygen concentration in the gas chamber or the oxygen pumping current is referred to the oxygen concentration in the detection gas atmosphere in order for comparison and judgment, whereby the disorder of the gas sensor element can be self-diagnosed. Thus, the operation state of the gas sensor can be always automatically monitored. In particular, when the invention is applied to a gas sensor for mounting on an automobile with severe environment, the reliability of the sensor is greatly improved. Furthermore, because according to the gas sensor of the invention, the oxygen concentration in the detection gas atmosphere can be directly measured, when the gas sensor is, for example, a $NO_x$ sensor for mounting on an automobile, the concentration of $NO_x$ and oxygen in the exhaust gases can be simultaneously measured.

DETAILED DESCRIPTION OF THE PREFERRED EMBODIMENTS

Figure 1:
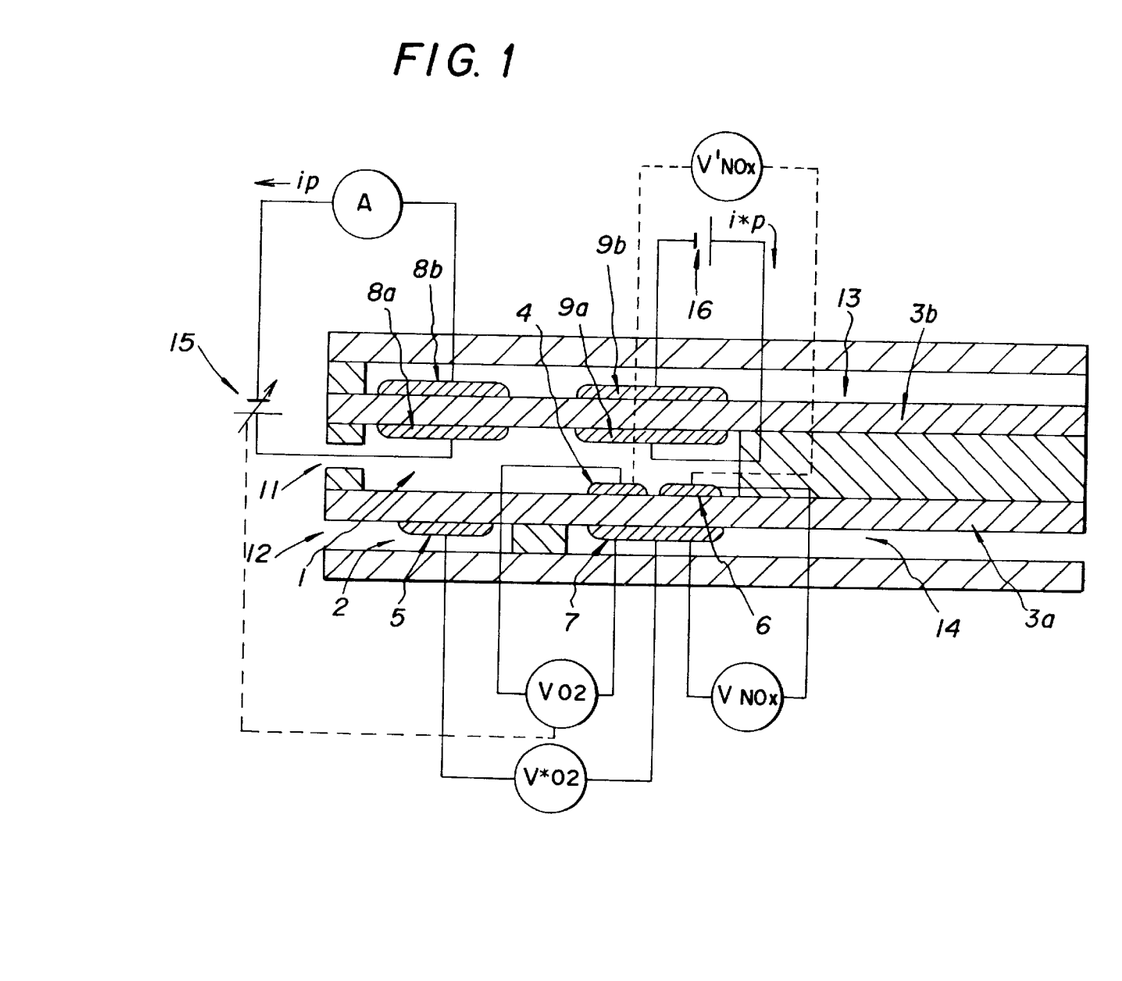
FIG. 1 is a cross-sectional structural view showing an embodiment of the sensor of the invention.

A fundamental structure of the gas sensor of the invention is shown in FIG. 1. The sensor structure comprising; a first gas chamber 1 formed by two oxygen ion conductive solid electrolyte substrates 3a, 3b; a first gas inlet 11 having a gas diffusion resistance for restraining the flow amount of gases entering the first gas chamber; a first oxygen sensing electrode 4 active only to oxygen, which is disposed on a surface of the first oxygen ion conductive solid electrolyte substrate 3a inside the first gas chamber; a gas sensing electrode 6 active to at least target gases and oxygen, which is disposed on the same surface of the first electrolyte substrate as for the first oxygen sensing electrode inside the first gas chamber; a reference electrode 7 active to oxygen, which is disposed on the first solid electrolyte substrate 3a such that it is brought into contact with an atmospheric air separated from the first gas chamber 1; an oxygen pump cell (8a, 8b) for controlling oxygen concentration in the first gas chamber, of which electrodes are made of materials active only to oxygen and disposed on the second solid electrolyte substrate 3b facing to the first solid electrolyte substrate; a gas reforming pump cell (9a, 9b) for chemically or electrochemically converting or decomposing the gases, of which a gas reforming electrode 9a is active to oxygen and the target gases and disposed on the second solid electrode substrate 3b in the first gas chamber so as to face to the gas sensing electrode 6, and a gas reforming counter electrode 9b is disposed on the second solid electrode substrate 3b outside the gas chamber such that it is brought into contact with the atmospheric air; and a second oxygen sensing electrode 5 active only to oxygen, which is disposed on the first solid electrolyte substrate such that it is directly exposed to the detection gas atmosphere.

The gas sensor of this structure is described in detail in the case of a combined $NO_x$ sensor which is a specific embodiment for use. The above-described $NO_x$ sensor shown in FIG. 1 can detect total $NO_x$ concentration in the exhaust gases of automobile.

First, reducing gases such as HC (hydrocarbon gases) and CO among $NO_x$ (NO and $NO_2$), HC, CO, $CO_2$, $SO_x$, $H_2O$, $O_2$, etc., which are contained in the exhaust gases diffusing and flowing in the first gas chamber 1 through the gas inlet 11, are oxidized to non-interference gases by pumping in and out oxygen through an air duct 13 using the oxygen pump cell and keeping the atmosphere inside the first gas chamber 1 at a predetermined oxygen concentration. Because the gas sensor is usually heated and operated at 500° C. or higher, the reducing gases such as HC and CO are instantly oxidized to non-interference gases such as $CO_2$ and $H_2O$ due to catalytic effects of the solid electrolyte constituting the gas chamber and the electrode materials.

Consequently, NO in the $NO_x$ is electrochemically converted into $NO_2$ by a $NO_x$ converting electrode which the gas reforming electrode 9a. The $NO_x$ converting electrode 9a is active to $NO_x$ and oxygen, and NO can be converted into $NO_2$ at least on the electrode. By using the $NO_x$ converting electrode 9a disposed in the first gas chamber 1 as a cathode, and the $NO_x$ converting counter electrode 9b disposed in the air duct 13 leading to the atmospheric air as an anode, and by applying a predetermined potential thereto, the gas sensor is operated. The $NO_x$ converting cell with the $NO_x$ converting electrode 9a and its counter electrode 9b is fundamentally the same as the oxygen pump cell (8a, 8b), but is different in the activity to $NO_x$ of the electrode disposed in the first gas chamber.

In succession, $NO_x$ converted into $NO_2$ by the $NO_x$ converting electrode is detected as a mixed potential by the $NO_x$ sensing electrode 6 facing to the $NO_x$ converting electrode. The output of $NO_x$ in this case is obtained by measuring a potential difference between the reference electrode 7 and the $NO_x$ sensing electrode 6 or a potential difference between the $No_x$ sensing electrode 6 and the first oxygen sensing electrode 4. That is, the total $NO_x$ concentrations in the exhaust gases can be detected by the sensor of the invention without any influence of the interference gases such as HC, etc.

Figure 2:
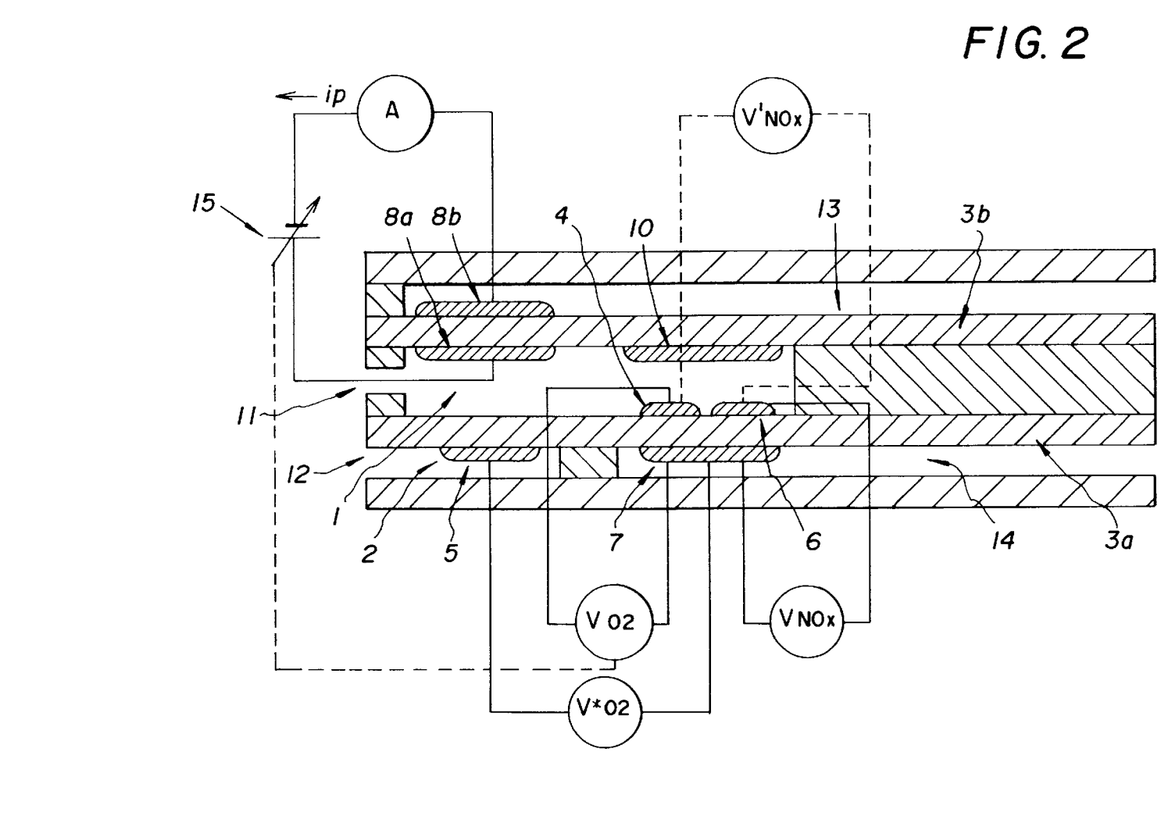
FIG. 2 is a cross-sectional structural view showing another embodiment of the sensor of the invention.

In the sensor structure shown in FIG. 2, a gas reforming catalyst layer 10 is disposed in place of the gas reforming pump cell. $NO_x$ in the exhaust gases can be converted to a NO gas as an equilibrium state for the detection of the total $NO_x$ by increasing the temperature of the sensor and setting the oxygen concentration at a low level. That is, the sensor has such an effect that $NO_x$ in the exhaust gases is converted into a NO gas in the first gas chamber 1. The converted NO is detected as a mixed potential by the above-described $NO_x$ sensing electrode 6. With regard to detecting the disorder of the sensor, in this case, it is the same as that of $NO_2$ sensing case.

As described above, in the sensor structure shown in FIG. 1 or FIG. 2, it is necessary to maintain the oxygen concentration in the first gas chamber 1 at a predetermined (oxygen) concentration of a several % level for oxidizing and removing the interference gases such as HC, etc. and obtain a reliable mixed potential output. For this purpose, an electromotive force due to the oxygen concentration difference between the oxygen sensing electrode 4 disposed in the first gas chamber 1 and the reference electrode 7 is detected, and the signal output 1 (the voltage output at $V_{O2}$ in the figures) is used for feedback-control of the driving voltage of the oxygen pump cell (8a, 8b). For example, when the oxygen concentration in the first gas chamber 1 is set up at 2%, the setting voltage is −43 mV at 600° C.

When the signal output 1 detecting the oxygen concentration in the first gas chamber 1 becomes an reliable state due to some disorder of the sensor, a large error occurs in the $NO_x$ concentration output of the $NO_x$ sensor. That is, in the case that the oxygen concentration in the first gas chamber 1 is abnormally lowered, the $NO_x$ sensing output is largely lowered because HC in the exhaust gases reaches the $NO_x$ sensing electrode without being sufficiently oxidized and removed. The $NO_2$ sensitivity of the $NO_x$ sensing electrode is also changed in proportion to the logarithm of the oxygen concentration. Accordingly, the disordered lowering of the oxygen concentration in the gas chamber 1 increases the $NO_x$ sensing output. On the other hand, in the case that the oxygen concentration in the first gas chamber 1 abnormally increases, the $NO_x$ sensing output is lowered owing to the dependence on oxygen concentrations. One of the causes of the disorder in the sensor described above is, for example, deterioration of the oxygen sensing electrodes 4, 5 by poisoning and so on. In this case, the oxygen pumping out or in is liable to occur excessively even in a predetermined oxygen concentration because the detection potential (signal output 1, 2 ), is changed. In the case that the gas tightness of the air duct 13 is lost, the oxygen pumping capability is lowered and the oxygen concentration in the first gas chamber does not reach a predetermined value. Furthermore, in the case that the gas tightness of an air duct 14 is lost, the potential of the reference electrode 7 is usually lowered depending on the oxygen concentration in the exhaust gases. Thus, an absolute value of the electromotive force between the reference electrode 7 and the oxygen sensing electrode 4 in the first gas chamber 1 is lowered resulting in disorder of controlling oxygen pumping.

Therefore, in the sensor structure of this invention shown in FIG. 1 or FIG. 2, the second oxygen sensing electrode 5 active only to oxygen is disposed on the first solid electrolyte substrate 3a, which is directly exposed to the detection gas atmosphere. The electromotive force (signal output 2) between the reference electrode 7 and the second oxygen sensing electrode 5 is detected as the oxygen concentration in the exhaust gas and compared with the above-described signal output 1 or the signal output of the pumping current of the oxygen pump cell, whereby the disorder of the sensor can be detected.

Figure 4:
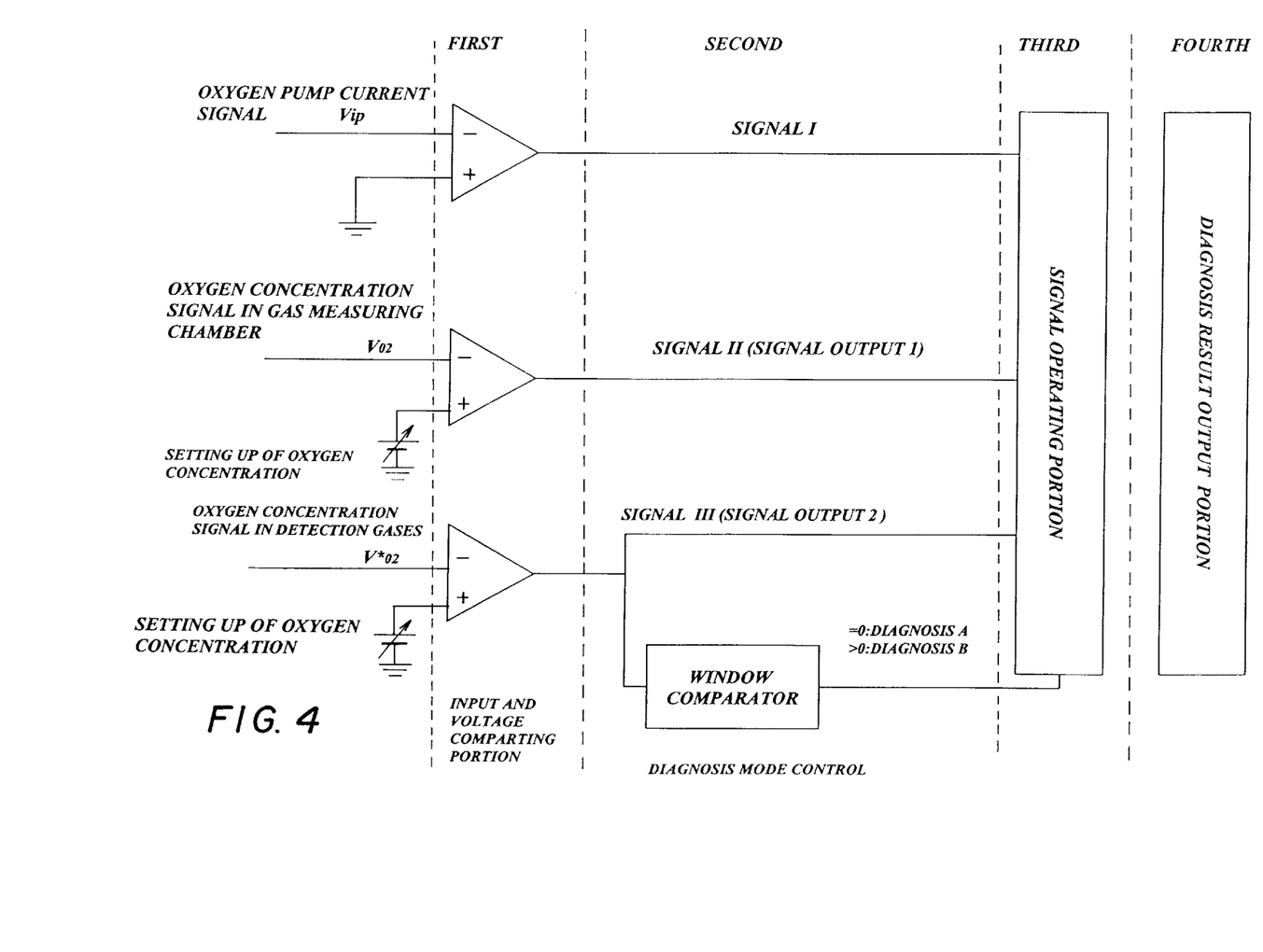
FIG. 4 is a circuit principle view showing an embodiment of the self-diagnosis method of the sensor of the invention.

In regard to a specific diagnosis method of the gas sensor carrying out the oxygen concentration control in the gas chamber 1 shown in FIG. 1 or FIG. 2, the circuit principle of diagnosis for detecting the disorder illustrated in FIG. 4 is proposed. The diagnosis circuit principle shown in FIG. 4 is constructed by four portions: the first portion is an input and voltage comparing portion; the second portion is a controlling portion for the diagnosis mode; the third portion is a signal operating portion; and the fourth portion is an output portion of diagnosis results. A current signal $V_{ip}$ of the oxygen pumping cell (8a, 8b) is defined as signal I; an oxygen concentration signal $V_{O2}$ in the first gas chamber 1 as signal II; and an oxygen concentration signal $V^*_{O2}$ in the detection gas atmosphere as signal III, respectively. When the oxygen concentration signal $V_{O2}$ in the first gas chamber 1 is equal to a predetermined setting value $V_s$, i.e., the output from a window-comparator is zero ($V_{O2}=V_s$) the diagnosis mode is defined as diagnosis-A.

On the other hand, when the oxygen concentration in the first gas chamber 1 is different from the predetermined setting value, i.e., the output from the window comparator is not zero ($V_{O2} \neq V_s$), the diagnosis mode is defined to be diagnosis-B. In the case of the diagnosis- A, when the pumping current of the oxygen pump is zero, and the oxygen concentration in the first gas chamber 1 is equal to that in the detection gases ($V_{O2}=V^*_{O2}$), the operation of the sensor system is judged to be in order. Notwithstanding the oxygen pumping current is zero, on the contrary, the operation of the sensor system is judged to be in disorder and the result is given when the oxygen concentration in the first gas chamber 1 is different from that in the detection gases ($V_{O2} \neq V^*_{O2}$). Similarly, notwithstanding the oxygen concentration $V_{O2}$ in the first gas chamber 1 is equal to the oxygen concentration in the detection gases ($V_{O2}=V^*_{O2}$), the operation of the sensor system is judged to be in disorder and the result is given when the oxygen pumping current is not zero.

Next, the cases of the diagnosis-B are considered. When the oxygen concentration signal $V_{O2}$ in the first gas chamber 1 is lower than a predetermined oxygen concentration setting value $V_s$, the oxygen pumping must be in the state of supplying oxygen into the first gas chamber 1. On the contrary, when the oxygen concentration signal $V_{O2}$ is higher than the setting value $V_s$, the oxygen pumping is in the state of evacuating oxygen from the first gas chamber 1. The diagnosis in which these oxygen pumping directions, the difference ($V_{O2}-V_s$) of the oxygen concentration signal in the gas chamber from the setting value, and the oxygen pumping current signal $V_{ip}$ are compared, is carried out to be judged as in order/disorder. These diagnosis operations can be put in practice using an analog circuit and more complicated diagnosis operations will be possible by using a microcomputer.

Figure 3:
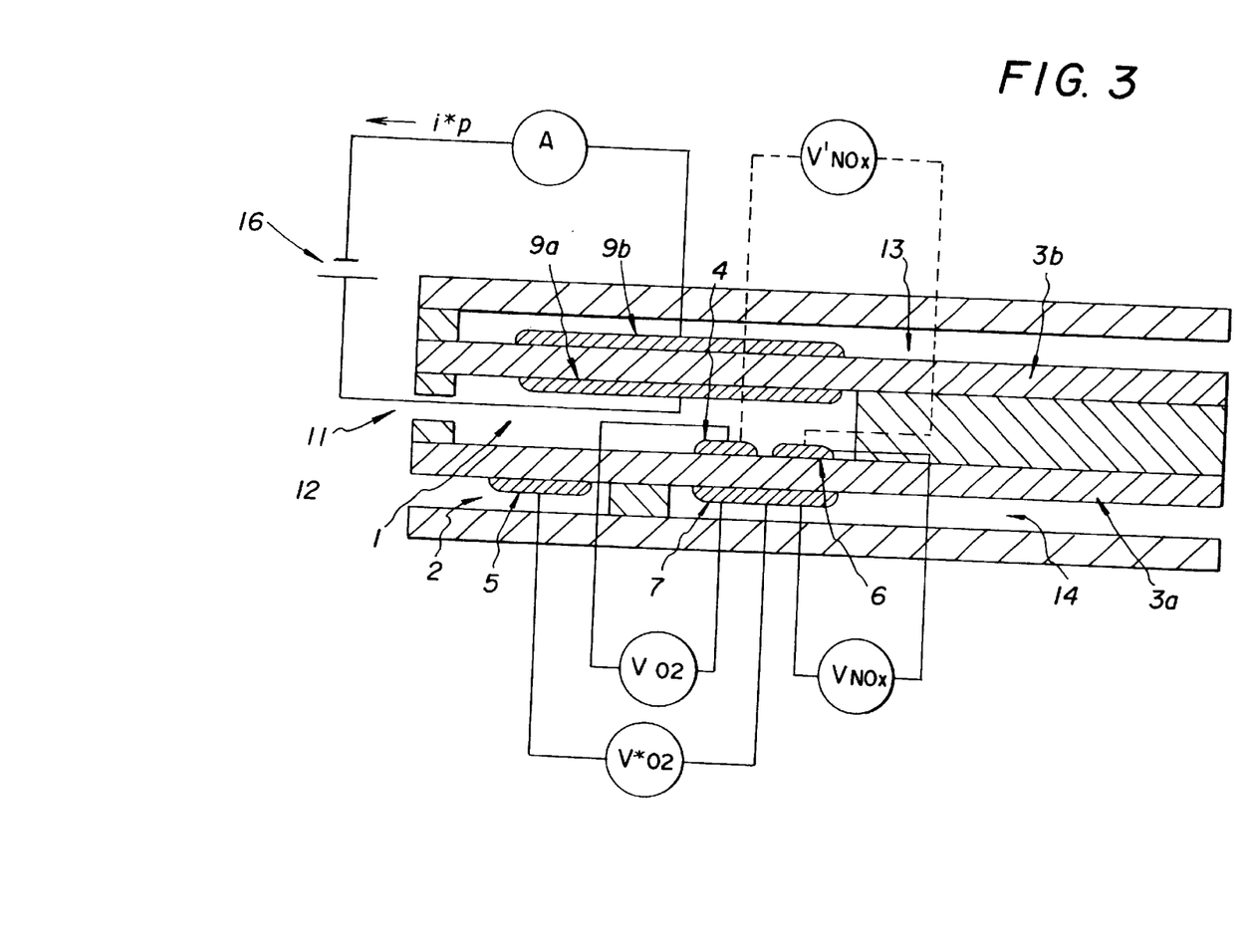
FIG. 3 is a cross-sectional structural view showing a still another embodiment of the sensor of the invention.

Another sensor structure of the invention is shown in FIG. 3. In this sensor structure, because the oxygen pump cell (8a, 8b) shown in FIG. 1 is eliminated, the oxygen pumping is given by the gas reforming pump cell (9a, 9b). Furthermore, other different point from the sensor structure of FIG. 1 is that the oxygen concentration signal in the first gas chamber 1 is not fed back for the control of oxygen concentration. That is, the oxygen pumping amount introduced is constant by the gas reforming pump cell.

In the sensor structure of FIG. 3, the oxygen concentration in the first gas chamber is influenced to some extent by the fluctuation of that in the exhaust gas because of having no oxygen control means. For this reason, in that sensor structure, it is not preferred to directly use a potential difference $V_{NOx}$ between the $NO_x$ sensing electrode 6 and the reference electrode 7 as the $NO_x$ sensing output. It is desirable to measure a potential difference $V'_{NOx}$ between the $NO_x$ sensing electrode 6 and the first oxygen sensing electrode 4. Alternatively, it is preferred to use a method of subtracting the potential difference $V_{O2}$ between the first oxygen sensing electrode 4 and the reference electrode 7 from the potential difference $V_{NOx}$ between the $NO_x$ sensing electrode 6 and the reference electrode 7.

The disorder in the sensor shown in FIG. 3 is fundamentally similar to that in the sensor shown in FIG. 1 or FIG. 2. However, in this sensor structure, because the oxygen pump cell (8a, 8b) for controlling the oxygen concentration is omitted, the oxygen pumping current $i_p$ cannot be used as the signal for the self-diagnosis. Thus, the self-diagnosis method of the sensor disorder in this structure is given as follows: $\delta V_{O2}$ obtained as a difference between the oxygen concentration signal $V_{O2}$ in the first gas chamber 1 and the oxygen concentration signal $V^*_{O2}$ in the second gas chamber 2 (oxygen concentration signal in the detection atmosphere) is compared with the setting value, whereby at least serious disorder can be detected. A fundamental embodiment of this self-diagnosis logic is shown in FIG. 5.

Figure 5:
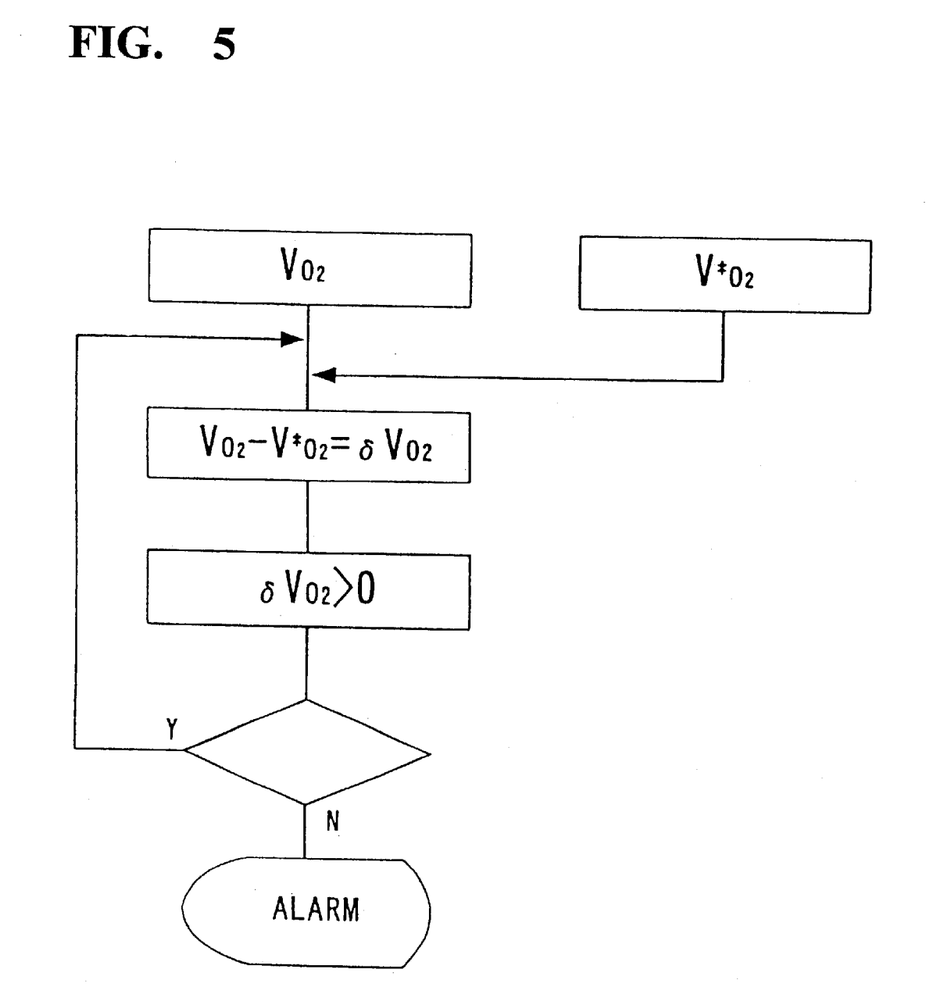
FIG. 5 is a diagnosis logic showing an embodiment of the self-diagnosis method of the sensor of the invention.
Figure 6:
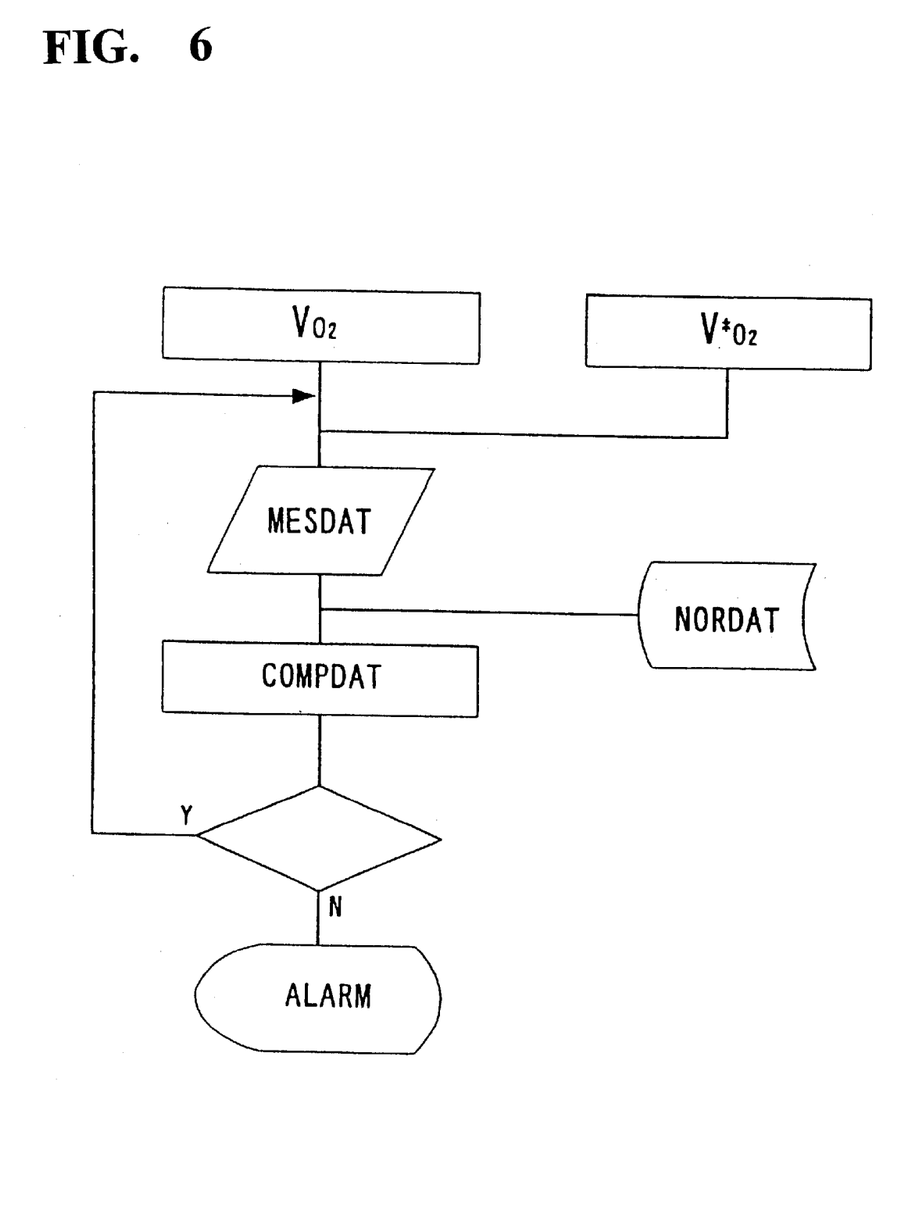
FIG. 6 is a diagnosis logic showing another embodiment of the self-diagnosis method of the sensor of the invention.
Figure 7:
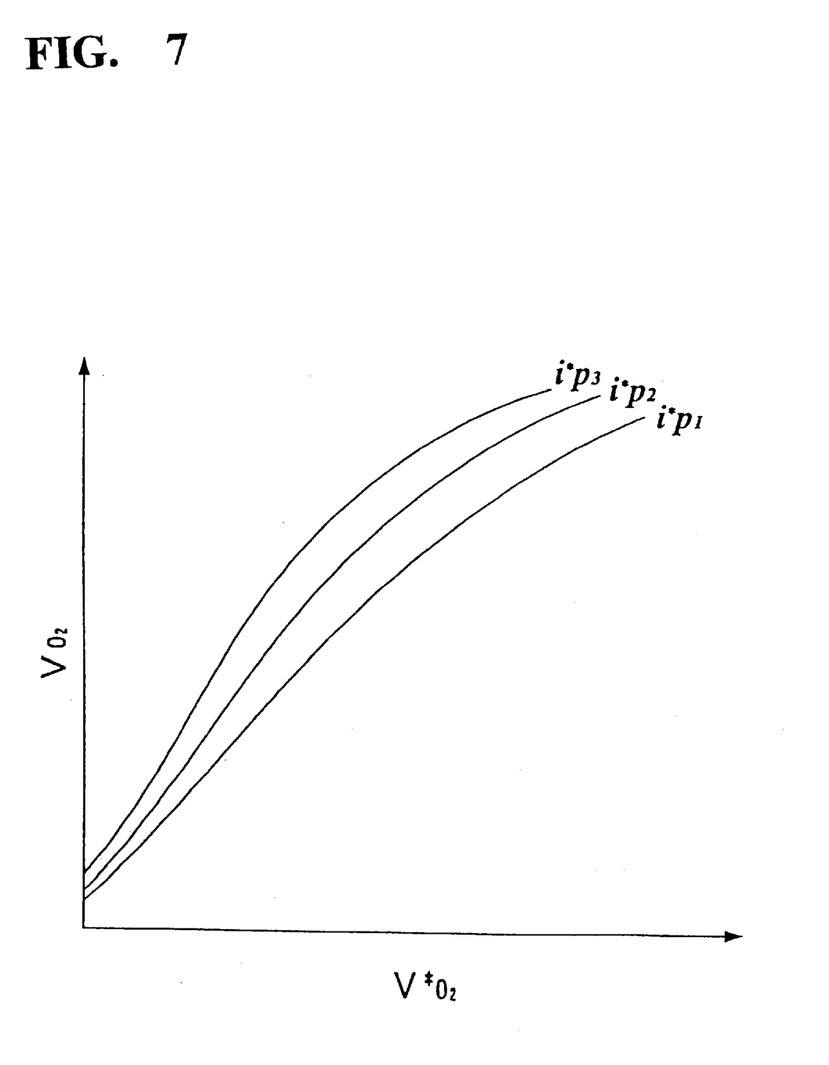
FIG. 7 is showing the characteristic curves used for the self-diagnosis method of the sensor of the invention.

However, it can be easily predicted that in the self-diagnosis logic as shown in FIG. 5, a little degradation in the gas sealing property is hard to be detected. Thus, the self-diagnosis logic shown in FIG. 6 is proposed. In this system, the oxygen concentration signal $V_{O2}$ in the first gas chamber 1 and the oxygen concentration signal $V^*_{O2}$ in the second gas chamber 2 (oxygen concentration signal in the detection atmosphere) are compared with map data at any time, and when the result is in a position out of a predetermined deviation amount, the sensor disorder is detected. That is, as shown in FIG. 6, $V_{O2}$ and $V^*_{O2}$ monitored at any time are subjected to a mapping treatment (MESDAT), and the position data are compared (COMPDAT) with map data (NORDAT) in a orderly state already memorized to determine the sensor disorder. For example, the map data (NORDAT) are obtained for the pumping current value ip of the $NO_x$ converting cell using $V_{O2}$ and $V^*_{O2}$ as variables as shown in FIG. 7. In the case that map data for $i^*_{p1}$ deviate from the area wherein a predetermined amount of error is allowed, the sensor disorder is detected.

Figure 8:
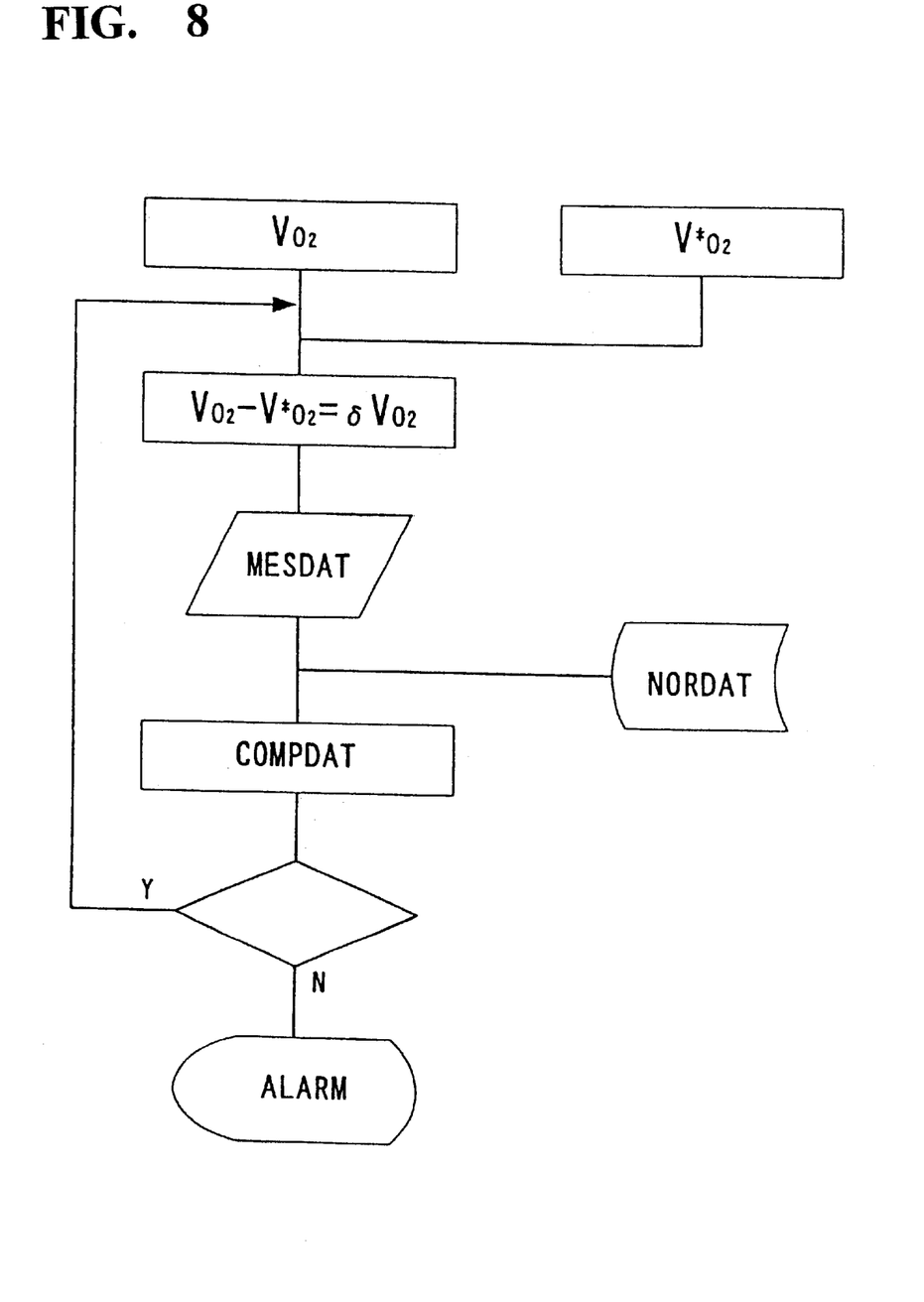
FIG. 8 is a diagnosis logic showing a still another embodiment of the self-diagnosis method of the sensor of the invention.
Figure 9:
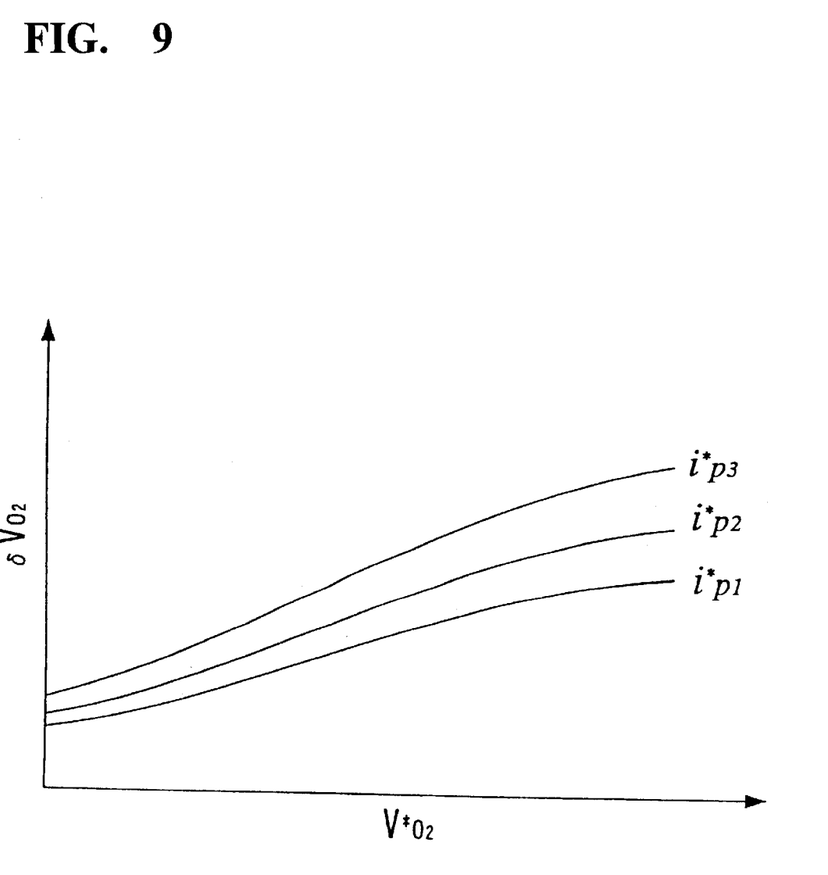
FIG. 9 is showing another characteristic curves used for the self-diagnosis method of the sensor of the invention.

By using similar map data, the gas tightness of the air duct, in which the reference electrode 7 is disposed, can be diagnosed. For example, as shown in FIG. 8, $\delta V_{O2}$ data obtained as a difference between the oxygen concentration signal $V_{O2}$ in the first gas chamber 1 and the oxygen concentration signal $V^*_{O2}$ in the second gas chamber 2 (oxygen concentration signal in the detection atmosphere) are obtained for $i^*_p$ with $V^*_{O2}$ as shown in FIG. 9. In the case that the map data for $i^*_{p1}$ deviate from the area that an error of a predetermined amount is allowed, the sensor disorder is detected.

It is obvious that the self-diagnosis method in the sensor structure shown in FIG. 3 can be applied to that of FIG. 1.

Furthermore, in the sensor structure of the invention, in addition that the measurement of the concentration of detection gases and the self-diagnosis of the sensor can be carried out, the oxygen concentration in the detection gas atmosphere is directly detected and can be utilized for other systems.

The cross-sectional structures of the sensors of the preferred embodiments of the invention are shown in FIG. 1 to FIG. 3. As a preferred manufacturing method of these sensors, green sheet lamination of oxygen ion conductive solid electrolyte is used. As the oxygen ion conductive solid electrolyte, yttria ($Y_2O_3$)-added zirconia is usually used. The amount of yttria additive is generally from 3 to 8 mol %. As the additive substance, magnesia (MgO), ceria (CeO), etc., may be used in place of yttria.

For the green sheet of zirconia, zirconia powder is first prepared as a raw material. The zirconia powder added predetermined amount of $Y_2O_3$, MgO, etc. is used.

In the case of manufacturing the sensors of FIG. 1 to FIG. 3, pastes for various electrodes (4, 5, 6, 7, 8a, 8b, 9a, 9b, 10) are coated on the zirconia green sheet by screen printing, etc. Lead conductors for taking out signals from the various electrodes, insulating layers, heaters, etc. are also separately formed by printing. After screen printing, the green sheets of the respective layers are laminated and pressed with heating. The laminated body is decreased at about 600° C. and sintered at 1,400° C. or higher. Finally, lead wires of Pt, etc., are welded to lead terminals, and the resulting sensor is provided for measurement.

The following materials are selected for the electrodes. For the oxygen sensing electrodes 4, 5, the reference electrode 7, the oxygen pump electrodes 8a, 8b, and the gas reforming counter electrode 9b, Pt active only to oxygen is used. It is essential that the gas reforming electrode 9a and the gas sensing electrode 6 have an activity to at least target gases and oxygen. In the case of the $NO_x$ sensor, Rh, Pt—Rh alloy, etc. are used for the gas reforming electrode ($NO_x$ converting electrode). For the $NO_x$ sensing electrode, various metal materials and metal oxide materials, such as Rh, Pt—Rh alloy, $NiCr_2O_4$, $MgCr_2O_4$, $Cr_2O_3$, etc., are used.

Figure 10:
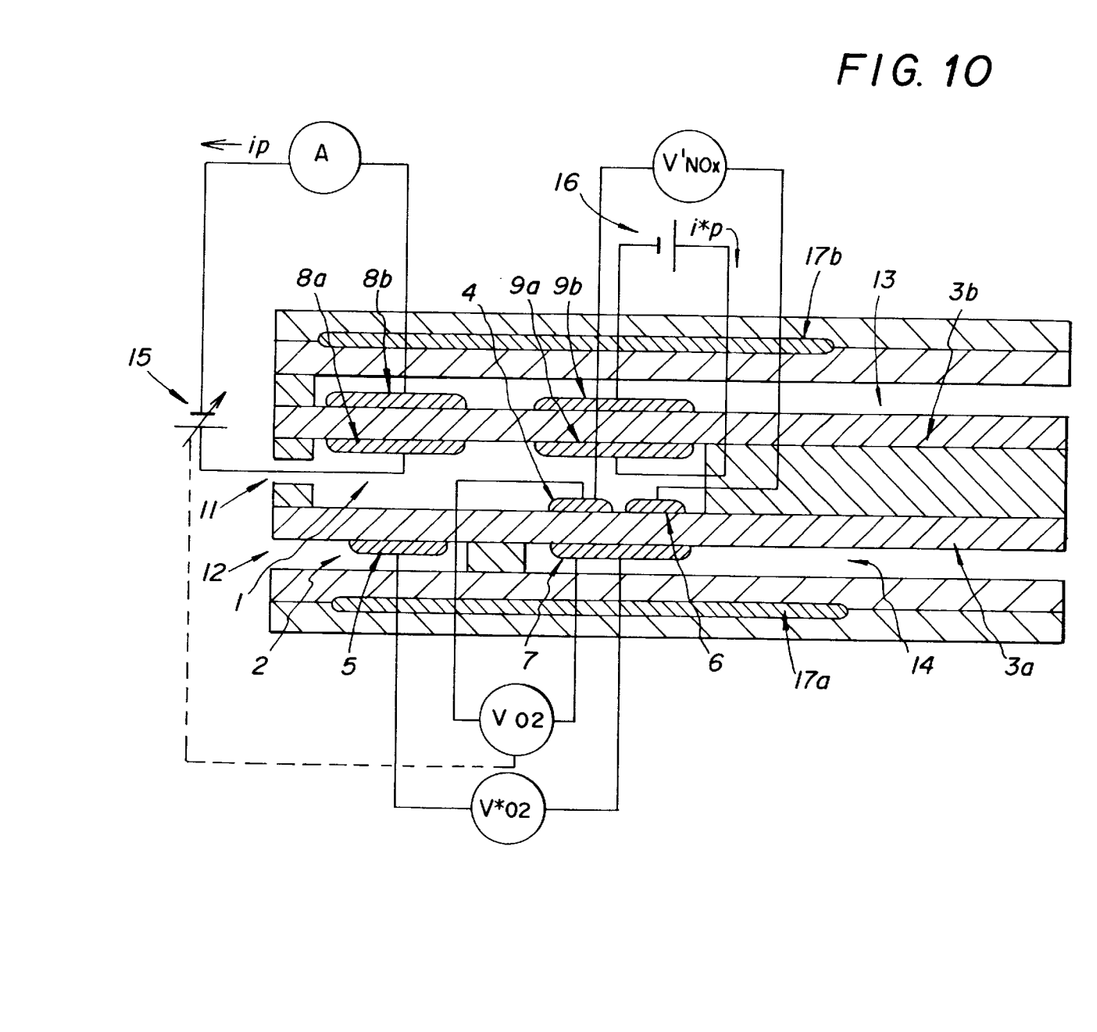
FIG. 10 is a cross-sectional structural view showing an even another embodiment of the sensor of the invention.

In the sensors of the structures shown in FIG. 1 to FIG. 3, a heating means is not shown, but in practically using the sensor, a heater substrate is usually added to those structures. From the viewpoints of heat transfer and temperature control, the heater substrate is desired to be bonded to the sensor substrate portion integratedly. Furthermore, from the viewpoints of the temperature distribution and relaxation of thermal strain in the laminated sensor structure, it is preferred to bond heater substrates on both the surfaces (upper and lower surfaces in the figure) of the sensor as shown in FIG. 10.

For the driving method of the sensors of the invention, a voltage variable-type DC power supply 15 is used for the oxygen pump cell as described above. The voltage of the power supply 15 is controlled by feeding back the electromotive force between the first oxygen sensing electrode 4 and the reference electrode 7.

On the other hand, the gas reforming pump cell is connected to a DC constant voltage power supply for constantly applying a predetermined voltage. Considering gas reforming and oxygen pumping capability, the optimum applied voltage is selected.

The various signals of the sensor of the invention except the pumping current are measured as the potential difference between the electrodes. The oxygen concentrations in the first gas chamber 1 and detection atmosphere (the second gas chamber 2) are measured as concentration electromotive forces generated between the oxygen sensing electrodes 4, 5 and the reference electrode 7 respectively. On the other hand, the potential difference between the gas sensing electrode 6 and the reference electrode 7 or the first oxygen sensing electrode 4 is due to a mixed potential. It must be considered that the concentration electromotive force is a potential difference due to concentration difference of the same kind of gas. For these potential measurements, as a simple method, a potentiometer (circuit) is used, and in this case, it is preferred from an accuracy standpoint that the potentiometer has an input impedance of at least three figures higher than the electrode impedance. On the other hand, the oxygen pumping current is measured by an ampere meter, but in the case of the present invention, the pumping current is taken out as the voltage signal.

The self-diagnosis method of the invention is explained in detail with reference to the following Examples.

EXAMPLE 1

A $NO_x$ sensor having a structure shown in FIG. 10 was prepared by a following method. Pt electrodes (4, 5, 7, 8a, 9b, 9b) and Pt—Rh alloy electrodes (6, 9a) were printed on green sheets of $Y_2O_3$-doped zirconia, followed by lamination and press into the above-described sensor structure. The laminated body was sintered at a temperature of 1,400° C. to prepare a sensor element. The sensor was heated and maintained at 600° C. by using heaters 17a, 17b, and $NO_x$ sensing outputs for detection gases having various oxygen and $NO_x$ concentrations were measured.

As the $NO_x$ output, a potential difference between the $NO_x$ sensing electrode 6 and the first oxygen sensing electrode 4 was measured. The results are shown in Table 1. In this case, the feed-back control of the oxygen concentration signal in the first gas chamber 1 to a variable power supply of an oxygen pump cell was carried out. Since the oxygen concentration in the first gas chamber was maintained at a predetermined oxygen concentration (in this case, 2.0%) even if the oxygen concentration in the detection gases was changed, it was confirmed that the influence of the interference gas (in this case, an oxygen gas) in the detection gases was restrained, and the measurement of the $NO_x$ concentration as carried out with high accuracy.

TABLE 1

| Oxygen concentration in detection gases (%) | $NO_x$ concentration in detection gases (ppm) | $NO_x$ sensing output (mV) |
| --- | --- | --- |
| 0.1 | 50 | 60 |
| 1.0 | 50 | 57 |
| 1.5 | 50 | 57 |
| 4.0 | 50 | 61 |
| 9.0 | 50 | 62 |
| 15.0 | 50 | 58 |
| 20.9 | 50 | 59 |

On the other hand, a self-diagnosis circuit of the principle shown in FIG. 4 was prepared and connected to the sensor together with a driving circuit and a measurement circuit of the sensor. For the case of making the oxygen concentration in the detection gases 2% equal to the setting oxygen concentration in the first gas chamber 1, the order/disorder diagnosis judgment was confirmed. That is, based on an electromotive force between the first oxygen sensing electrode 4 and the reference electrode 7, the oxygen pump cell-(8a, 8b) is driven so that the oxygen concentration in the first gas chamber 1 is always 2%. Accordingly, it becomes unnecessary to have oxygen pump cell work when the oxygen concentration in the first gas chamber 1 is 2%. At the same time, it can be found that the oxygen concentration in the detection gases is 2% from an electromotive force between the second oxygen sensing electrode 5 and the reference electrode 7. In this case, the oxygen pumping current becomes zero. It was confirmed from the signal output of the diagnosis circuit, therefore, that the first oxygen sensing electrode 4 in the first gas chamber 1 and the oxygen pumping cell are worked in order.

EXAMPLE 2

A NO sensor similar to that in Example 1 was prepared and connected with the above-described self-diagnosis circuit. The oxygen concentration in the detection gases was set to 0.1%. In this case, it was confirmed from the output signal of the diagnosis circuit that the output current of the oxygen pump flew at about 400 μA in the positive direction so as to supply the oxygen to the gas chamber 1. However, the potential of the first oxygen sensing electrode in the first gas chamber 1 did not increase to the potential corresponding to 2% of the redetermined oxygen concentration, that is, the disorder of the sensor was shown. As the result of detailed inspection, cracking was found at a part of the zirconia substrate of the sensor element.

What is claimed is:

1. A combined gas sensor comprising:

a first gas chamber formed by first and second oxygen ion conductive solid electrolytes;

a first gas inlet having a diffusion resistance for restricting a flow amount of gases entering the first gas chamber;

a first oxygen sensing electrode active only to oxygen, which is disposed on a surface of the first oxygen ion conductive solid electrolyte substrate inside the first gas chamber;

a gas sensing electrode active to at least target gases and oxygen, which is disposed on the same surface of the first electrolyte substrate as the first oxygen sensing electrode inside the first gas chamber;

a reference electrode active to oxygen, which is disposed on the first solid electrolyte substrate such that it is brought into contact with an atmospheric air separated from the first gas chamber;

an oxygen pump cell for controlling oxygen concentration in the first gas chamber, of which electrodes are made of materials active only to oxygen and disposed on the second solid electrolyte substrate facing to the first solid electrolyte substrate;

a gas reforming pump cell for electrochemically converting or decomposing the gases, of which a gas reforming electrode is active to oxygen and the target gases, and disposed on the second solid electrolyte substrate inside the first gas chamber so as to face the gas sensing electrode, and a gas reforming counter electrode disposed on the second solid electrolyte substrate outside the gas chamber such that it is brought into contact with the atmospheric air; and a second oxygen sensing electrode active only to oxygen, which is disposed on the first solid electrolyte substrate such that it is directly exposed to a detection gas atmosphere.

2. The combined gas sensor according to claim 1, wherein the second oxygen sensing electrode active only to oxygen, which is disposed on the first solid electrolyte substrate such that it is directly exposed to the detection gas atmosphere, is disposed in a second gas chamber having a gas inlet and being adjacent to an air duct in which the reference electrode is disposed, and the oxygen concentration in the detection gas atmosphere is measured using concentration electromotive force between said second oxygen sensing electrode and said reference electrode.

3. The combined gas sensor according to claim 1, wherein the target gases are nitrogen oxides made of NO and $NO_2$ as main constituents.

4. A combined gas sensor comprising:

a first gas chamber formed by first and second oxygen ion conductive solid electrolytes;

a first gas inlet having a diffusion resistance for restricting a flow amount of gases entering the first gas chamber;

a first oxygen sensing electrode active only to oxygen, which is disposed on a surface of the first oxygen ion conductive solid electrolyte substrate inside the first gas chamber;

a gas sensing electrode active to at least target gases and oxygen, which is disposed on the same surface of the first electrolyte substrate as the first oxygen sensing electrode inside the first gas chamber;

a reference electrode active to oxygen, which is disposed on the first solid electrolyte substrate such that it is brought into contact with an atmospheric air separated from the first gas chamber;

a gas reforming pump cell for electrochemically converting or decomposing the gases, of which a gas reforming electrode is active to oxygen and the target gases and disposed on the second solid electrolyte substrate inside the first gas chamber so as to face the gas sensing electrode, and a gas reforming counter electrode disposed on the second solid electrolyte substrate outside the first gas chamber such that it is brought into contact with the atmospheric air; and a second oxygen sensing electrode active only to oxygen, which is disposed on the first solid electrolyte substrate such that it is directly exposed to a detection gas atmosphere.

5. The combined gas sensor according to claim 4, wherein the second oxygen sensing electrode active only to oxygen, which is disposed on the first solid electrolyte substrate such that it is directly exposed to the detection gas atmosphere, is disposed in a second gas chamber having a gas inlet and being adjacent to an air duct in which the reference electrode is disposed, and the oxygen concentration in the detection gas atmosphere is measured using concentration electromotive force between said second oxygen sensing electrode and said reference electrode.

6. The combined gas sensor according to claim 4 wherein the target gases are nitrogen oxides made of NO and $NO_2$ as main constituents.

7. A combined gas sensor comprising:

an oxygen pump cell for controlling oxygen concentration in a first gas chamber, of which electrodes are made of materials active only to oxygen and disposed on a second solid electrolyte substrate facing a first solid electrolyte substrate;

an oxygen sensing cell comprising a first oxygen sensing electrode active only to oxygen, which is disposed on a surface of the first solid electrolyte substrate in the gas chamber and a reference electrode which is disposed on the first solid electrolyte substrate such that it is brought into contact with an atmospheric air separated from the first gas chamber; and a gas reforming pump cell for electrochemically converting or decomposing target gases, of which a gas reforming electrode active to oxygen and the target gases is disposed on the second solid electrolyte substrate in the gas chamber so as to face a gas sensing electrode, and a gas reforming counter electrode is disposed on the second solid electrolyte substrate outside the gas chamber such that it is brought into contact with an atmospheric air, and a second oxygen sensing electrode active only to oxygen, which is disposed on the first solid electrolyte substrate such that it is directly exposed to a detection gas atmosphere; and characterized by having a cell driving circuit wherein a DC variable power supply for controlling the oxygen concentration in the gas chamber at a constant level by feed-back control of pumping currents to an applied voltage of the oxygen pump cell according to an electromotive force between the first oxygen sensing electrode and the reference electrode being as a signal output is connected to the oxygen pump cell, and a DC constant voltage power supply for making an oxygen pumping current of the gas reforming pump cell constant and making an electrochemical decomposition or conversion amount of the target gas constant is connected to the gas reforming pump cell.

8. The combined gas sensor according to claim 7, wherein the oxygen concentration in the detection gas atmosphere is directly measured by the electromotive force between the second oxygen sensing electrode and the reference electrode, such that self-diagnosis of sensor disorder can be carried out using a signal output of said oxygen concentration.

9. The combined gas sensor according to claim 7, wherein a signal output due to the oxygen concentration in the detection gas atmosphere, the signal output due to the oxygen concentration in the first gas chamber, a pumping current of the oxygen pump cell, and a pumping current of the gas reforming cell can be detected as voltage signals, and self diagnosis of disorder of the oxygen sensing cell with the first oxygen sensing electrode and the reference electrode, the oxygen pump cell, and the gas reforming pump cell, or the gas tightness of the gas chamber and the air duct, can be carried out by comparative operations among said voltage signals.

10. The combined gas sensor according to claim 7, wherein the gas sensor has means for self-diagnosis of disorder of the oxygen sensing cell with the first oxygen sensing electrode and the reference electrode, the oxygen pump cell, and the gas reforming pump cell, or about gas tightness of the gas chamber and the air duct, and said self-diagnosis can be carried out from a comparison and judgment of a signal output due to the oxygen concentration in the detection atmosphere, detection data using said signal output, and previously memorized map data.

11. A combined gas sensor comprising:

an oxygen pump cell for controlling oxygen concentration in a gas chamber, of which electrodes are made of materials active only to oxygen and disposed on a second solid electrolyte substrate facing a first solid electrolyte substrate;

a first oxygen sensing cell comprising a first oxygen sensing electrode active only to oxygen, which is disposed on a surface of the first solid electrolyte substrate in the gas chamber and a reference electrode which is disposed on the first solid electrolyte substrate such that it is brought into contact with an atmospheric air separated from the gas chamber;

a gas reforming means for electrochemically converting or decomposing target gases;

a second oxygen sensing cell comprising a second oxygen sensing electrode active only to oxygen, which is disposed on the first solid electrolyte substrate such that it is directly exposed to a detection gas atmosphere and said reference electrode;

a gas sensing cell comprising a gas sensing electrode active to at least target gases and oxygen, which is disposed on the same surface of the first electrolyte substrate as the first oxygen sensing electrode inside the gas chamber;

a cell driving circuit connected to the oxygen pump cell, wherein a DC variable power supply for controlling the oxygen concentration in the gas chamber at a constant level by feed-back control of pumping currents to an applied voltage of the oxygen pump cell according to an electromotive force between the first oxygen sensing electrode and the reference electrode being as a signal output; and a self-diagnosis means for comparing a current signal of said oxygen pump cell, a first oxygen concentration signal in said gas chamber detected by said first oxygen sensing cell and/or a second oxygen concentration signal in said detection gas atmosphere detected by said second oxygen sensing cell with a map data predetermined from a first oxygen concentration signal in said gas chamber detected by said first oxygen sensing cell and a second oxygen concentration signal in said detection gas atmosphere detected by said second oxygen sensing cell to judge a disorder of the sensor.

12. The combined gas sensor according to claim 11, wherein said self-diagnosis means comprises:

an input and voltage comparing portion connected with said current signal of said oxygen pump cell, said first oxygen concentration signal in said gas chamber detected by said first oxygen sensing cell and said second oxygen concentration signal in said detection gas atmosphere detected by said second oxygen sensing cell;

a controlling portion for a diagnosis mode;

a signal operation portion, in which said map data is memorized; and an output portion of diagnosis results.

13. The combined gas sensor according to claim 11, wherein:

said gas reforming means comprises a gas reforming electrode active to oxygen and the target gases disposed on the second solid electrolyte substrate in the gas chamber so as to face a gas sensing electrode, and a gas reforming counter electrode disposed on the second solid electrolyte substrate outside the gas chamber such that it is brought into contact with an atmospheric air.

14. A combined gas sensor comprising:

a gas reforming pump cell for electrochemically converting or decomposing target gases, of which a gas reforming electrode active to oxygen and the target gases is disposed on a second solid electrolyte substrate in a gas chamber so as to face a gas sensing electrode, and a gas reforming counter electrode is disposed on the second solid electrolyte substrate outside the gas chamber such that it is brought into contact with an atmospheric air;

a first oxygen sensing cell comprising a first oxygen sensing electrode active only to oxygen, which is disposed on a surface of a first solid electrolyte substrate in the gas chamber and a reference electrode which is disposed on the first solid electrolyte substrate such that it is brought into contact with an atmospheric air-separated from the gas chamber;

a second oxygen sensing cell comprising a second oxygen sensing electrode active only to oxygen, which is disposed on the first solid electrolyte substrate such that it is directly exposed to a detection gas atmosphere and said reference electrode;

a gas sensing cell comprising a gas sensing electrode active to at least target gases and oxygen, which is disposed on the same surface of the first electrolyte substrate as the first oxygen sensing electrode inside the gas chamber; and a self-diagnosis means for comparing a pumping current value of said gas reforming pump cell, a first oxygen concentration signal in said gas chamber detected by said first oxygen sensing cell and/or a second oxygen concentration signal in said detection gas atmosphere detected by said second oxygen sensing cell, with a map data predetermined from a first oxygen concentration signal in said gas chamber detected by said first oxygen sensing cell and a second oxygen concentration signal in said detection gas atmosphere detected by said second oxygen sensing cell to judge a disorder of the sensor.

15. The combined gas sensor according to claim 14, wherein said self-diagnosis means comprises:

an input and voltage comparing portion connected with said current signal of said gas reforming pump cell, said first oxygen concentration signal in said gas chamber detected by said first oxygen sensing cell and said second oxygen concentration signal in said detection gas atmosphere detected by said second oxygen sensing cell;

a controlling portion for a diagnosis mode;

a signal operation portion, in which said map data is memorized; and an output portion of diagnosis results.

* * * * *